(12) United States Patent
Hiramatsu et al.

(10) Patent No.: US 10,631,552 B2
(45) Date of Patent: Apr. 28, 2020

(54) LACTIC ACID BACTERIA-FERMENTED SOYBEAN FOODSTUFF, AND LACTIC ACID BACTERIA FOR LACTIC ACID BACTERIA-FERMENTED SOYBEAN FOODSTUFF

(71) Applicant: PELICAN CORPORATION, Saitama (JP)

(72) Inventors: Akinori Hiramatsu, Saitama (JP); Hiroshi Harada, Saitama (JP)

(73) Assignee: PELICAN CORPORATION, Saitama (JP)

( * ) Notice: Subject to any disclaimer, the term of this patent is extended or adjusted under 35 U.S.C. 154(b) by 0 days.

(21) Appl. No.: 16/073,067

(22) PCT Filed: Mar. 21, 2017

(86) PCT No.: PCT/JP2017/011098
§ 371 (c)(1),
(2) Date: Jul. 26, 2018

(87) PCT Pub. No.: WO2017/164146
PCT Pub. Date: Sep. 28, 2017

(65) Prior Publication Data
US 2019/0029282 A1    Jan. 31, 2019

(30) Foreign Application Priority Data
Mar. 24, 2016   (JP) .................. 2016-060338

(51) Int. Cl.
| | |
|---|---|
| *A23C 11/10* | (2006.01) |
| *C12N 1/20* | (2006.01) |
| *A23L 11/00* | (2016.01) |
| *A23C 20/02* | (2006.01) |
| *A23L 2/38* | (2006.01) |
| *C12R 1/46* | (2006.01) |
| *A23C 23/00* | (2006.01) |

(52) U.S. Cl.
CPC ............ *A23C 11/106* (2013.01); *A23C 11/10* (2013.01); *A23C 20/025* (2013.01); *A23L 2/382* (2013.01); *A23L 11/00* (2016.08); *C12N 1/20* (2013.01); *C12R 1/46* (2013.01); *A23C 23/00* (2013.01); *A23Y 2240/75* (2013.01)

(58) Field of Classification Search
CPC ............ A23C 11/106; C12R 1/46; C12N 1/20
USPC .......................................................... 426/49
See application file for complete search history.

(56) References Cited

U.S. PATENT DOCUMENTS 3,944,676 A * 3/1976 Fridman .............. A23C 20/025
426/46
2016/0044931 A1    2/2016 Kaneko et al.

FOREIGN PATENT DOCUMENTS

| AU | 2014250456 A1 | 11/2015 |
|---|---|---|
| CN | 105101813 A | 11/2015 |
| EP | 2992765 A1 | 3/2016 |
| JP | 14-163123 A1 | 2/2017 |
| KR | 10 2015 0138846 A | 12/2015 |
| WO | 2014/091899 A1 | 6/2014 |
| WO | 2014/163123 A1 | 10/2014 |

OTHER PUBLICATIONS

Masako Ito et al., Making Novel Fermented Food from Soy-milk, Aichi Industrial Technology Institute Kenkyu Hokoku 2006, No. 5, Dec. 2006, pp. 144-145.

* cited by examiner

*Primary Examiner* — Hamid R Badr
(74) *Attorney, Agent, or Firm* — McGlew and Tuttle, P.C.

(57) ABSTRACT

Provided are a lactic acid bacterium for a lactic acid bacterium-fermented soybean foodstuff, which takes a short fermentation time even when applied to a soybean raw material and has a wide optimal temperature range, and hence can cause curdling in a short period of time even at low temperature, thus being extremely suited for fermentation of the soybean raw material, a lactic acid bacterium-fermented soybean foodstuff comprising the lactic acid bacterium, and a production method for a lactic acid bacterium-fermented soybean foodstuff. The lactic acid bacterium-fermented soybean foodstuff comprises a lactic acid bacterium belonging to *Streptococcus thermophilus* and having an accession number of NITE BP-02207. The lactic acid bacterium-fermented soybean foodstuff of the present invention is preferably a soybean yogurt lactic acid bacterium-fermented soybean foodstuff.

4 Claims, 2 Drawing Sheets
Specification includes a Sequence Listing.

SEQUENCE LISTING

```
<160> NUMBER OF SEQ ID NOS: 1

<210> SEQ ID NO 1
<211> LENGTH: 1471
<212> TYPE: DNA
<213> ORGANISM: Streptococcus thermophilus

<400> SEQUENCE: 1
ggacgaacgc tggcggcgtg cctaatacat gcaagtagaa cgctgaagag aggagcttgc      60
tcttcttgga tgagttgcga acgggtgagt aacgcgtagg taacctgcct tgtagcgggg     120
gataactatt ggaaacgata gctaataccg cataacaatg gatgacacat gtcatttatt     180 tgaaagggc  aattgctcca ctacaagatg gacctgcgtt gtattagcta gtaggtgagg     240
taatggctca cctaggcgac gatacatagc cgacctgaga gggtgatcgg ccacactggg     300
actgagacac ggcccagact cctacgggag gcagcagtag ggaatcttcg gcaatggggg     360
caaccctgac cgagcaacgc cgcgtgagtg aagaaggttt tcggatcgta aagctctgtt     420
gtaagtcaag aacgggtgtg agagtggaaa gttcacactg tgacggtagc ttaccagaaa     480
gggacggcta actacgtgcc agcagccgcg gtaatacgta ggtcccgagc gttgtccgga     540
tttattgggc gtaaagcgag cgcaggcggt ttgataagtc tgaagttaaa ggctgtggct     600
caaccatagt tcgctttgga aactgtcaaa cttgagtgca gaaggggaga gtggaattcc     660
atgtgtagcg gtgaaatgcg tagatatatg gaggaacacc ggtggcgaaa gcggctctct     720
ggtctgtaac tgacgctgag gctcgaaagc gtggggagcg aacaggatta gataccctgg     780
tagtccacgc cgtaaacgat gagtgctagg tgttggatcc tttccgggat tcagtgccgc     840
agctaacgca ttaagcactc cgcctgggga gtacgaccgc aaggttgaaa ctcaaaggaa     900
ttgacggggg cccgcacaag cggtggagca tgtggtttaa ttcgaagcaa cgcgaagaac     960
cttaccaggt cttgacatcc cgatgctatt tctagagata gaaagttact tcggtacatc    1020
ggtgacaggt ggtgcatggt tgtcgtcagc tcgtgtcgtg agatgttggg ttaagtcccg    1080
caacgagcgc aaccccctatt gttagttgcc atcattcagt tgggcactct agcgagactg    1140
ccggtaataa accggaggaa ggtggggatg acgtcaaatc atcatgcccc ttatgacctg    1200
```

```
ggctacacac gtgctacaat ggttggtaca acgagttgcg agtcggtgac ggcgagctaa    1260
tctcttaaag ccaatctcag ttcggattgt aggctgcaac tcgcctacat gaagtcggaa    1320
tcgctagtaa tcgcggatca gcacgccgcg gtgaatacgt tcccgggcct tgtacacacc    1380
gcccgtcaca ccacgagagt ttgtaacacc cgaagtcggt gaggtaacct tttggagcca    1440
gccgcctaag gtgggacaga tgattggggt g                                   1471
```

LACTIC ACID BACTERIA-FERMENTED SOYBEAN FOODSTUFF, AND LACTIC ACID BACTERIA FOR LACTIC ACID BACTERIA-FERMENTED SOYBEAN FOODSTUFF

TECHNICAL FIELD

The present invention relates to a lactic acid bacterium for a lactic acid bacterium-fermented soybean foodstuff, a lactic acid bacterium-fermented soybean foodstuff comprising the lactic acid bacterium, and a production method therefor.

BACKGROUND ART

A foodstuff using soybeans as a raw material, such as soy milk, is rich in dietary fiber and has a high nutritional value, and hence is attracting attention from a viewpoint of health as well. A beverage is a general application method for soy milk. As an application method for soy milk other than the beverage, in Non Patent Document 1, there is proposed production of a fermented foodstuff obtained by fermenting soy milk into a yogurt form with existing lactic acid bacteria. In addition, in Patent Document 1, there is proposed a fermented foodstuff obtained by fermenting powdered soy milk using soybean flour as a raw material with lactic acid bacteria. However, in Non Patent Document 1, 8 hours or more of the fermentation is required in order to obtain the fermented foodstuff of a yogurt form, and in Patent Document 1, the fermentation is performed for 12 hours or more. That is, when soybeans are used as a raw material, a long fermentation time is needed in order to obtain the fermented foodstuff of a yogurt form. When a long fermentation time is needed as described above, there is a problem in that application to a commercial production line is difficult.

Further, a commercially available fermented soybean foodstuff does not curdle without a thickener, and hence needs the thickener. However, there is a problem in that incorporation of the thickener degrades qualities, such as taste, sourness, and smoothness.

PRIOR ART DOCUMENTS

Patent Document

Patent Document 1: WO/2014/091899 A1

Non Patent Document

Non Patent Document 1: Masako Ito, Masahiro Kojima, Miyuki Yano, and Shigezo Naito (2006), Making Novel Fermented Food from Soy-milk, Research Report of Food Research Center, Aichi Prefecture

SUMMARY OF THE INVENTION

Problems to be Solved by the Invention

The present invention has been made in view of the problems of the related art described above, and an object of the present invention is to provide a lactic acid bacterium for a lactic acid bacterium-fermented soybean foodstuff, which takes a short fermentation time even when applied to a soybean raw material and has a wide optimal temperature range, and hence can cause curdling in a short period of time even at low temperature, thus being extremely suited for fermentation of the soybean raw material, a lactic acid bacterium-fermented soybean foodstuff comprising the lactic acid bacterium, and a production method for a lactic acid bacterium-fermented soybean foodstuff.

Means for Solving Problems

In order to achieve the above-mentioned object, the inventors of the present invention have made extensive investigations on lactic acid bacteria suited for fermentation of a material using soybeans as a raw material, such as soy milk or soybean flour, and as a result, have found that a novel lactic acid bacterium belonging to *Streptococcus thermophilus* is extremely suited for fermentation of soybeans. That is, a lactic acid bacterium-fermented soybean foodstuff according to the present invention comprises a lactic acid bacterium belonging to *Streptococcus thermophilus* and having an accession number of NITE BP-02207.

The lactic acid bacterium-fermented soybean foodstuff according to the present invention is preferably a yogurt-like lactic acid bacterium-fermented soybean foodstuff.

A production method for a lactic acid bacterium-fermented soybean foodstuff according to the present invention comprises a step of fermenting with a lactic acid bacterium belonging to *Streptococcus thermophilus* and having an accession number of NITE BP-02207.

A lactic acid bacterium for a lactic acid bacterium-fermented soybean foodstuff according to the present invention is a lactic acid bacterium belonging to *Streptococcus thermophilus* and having an accession number of NITE BP-02207.

Advantageous Effects of the Invention

The present invention has the following significant effects: the lactic acid bacterium for a lactic acid bacterium-fermented soybean foodstuff, which takes a short fermentation time even when applied to a soybean raw material and has a wide optimal temperature range, and hence can cause curdling in a short period of time even at low temperature, thus being extremely suited for fermentation of the soybean raw material, and the lactic acid bacterium-fermented soybean foodstuff comprising the lactic acid bacterium can be provided.

Further, the lactic acid bacterium of the present invention has high fermentative activity not only under an anaerobic condition but also under an aerobic condition. In addition, according to the lactic acid bacterium of the present invention, curdling can be caused without using a thickener, and hence an edible lactic acid bacterium-fermented soybean foodstuff significantly improved also in taste evaluation for flavor, smooth texture, and the like can be produced. In addition, the lactic acid bacterium-fermented soybean foodstuff of the present invention also exhibits the following effect: when a certain degree of acidity is reached, the lactic acid bacterium falls into a dormant state, and hence, even after several months, the sourness (acidity) remains unchanged and the foodstuff does not spoil. Moreover, yogurt generally uses two or more kinds of bacteria as a mixture. In this regard, the lactic acid bacterium of the present invention has a wide optimal temperature range, and hence can adapt to the optimal temperatures of other bacteria. Accordingly, it can be expected for future applications.

MODES FOR CARRYING OUT THE INVENTION

Figure 1:
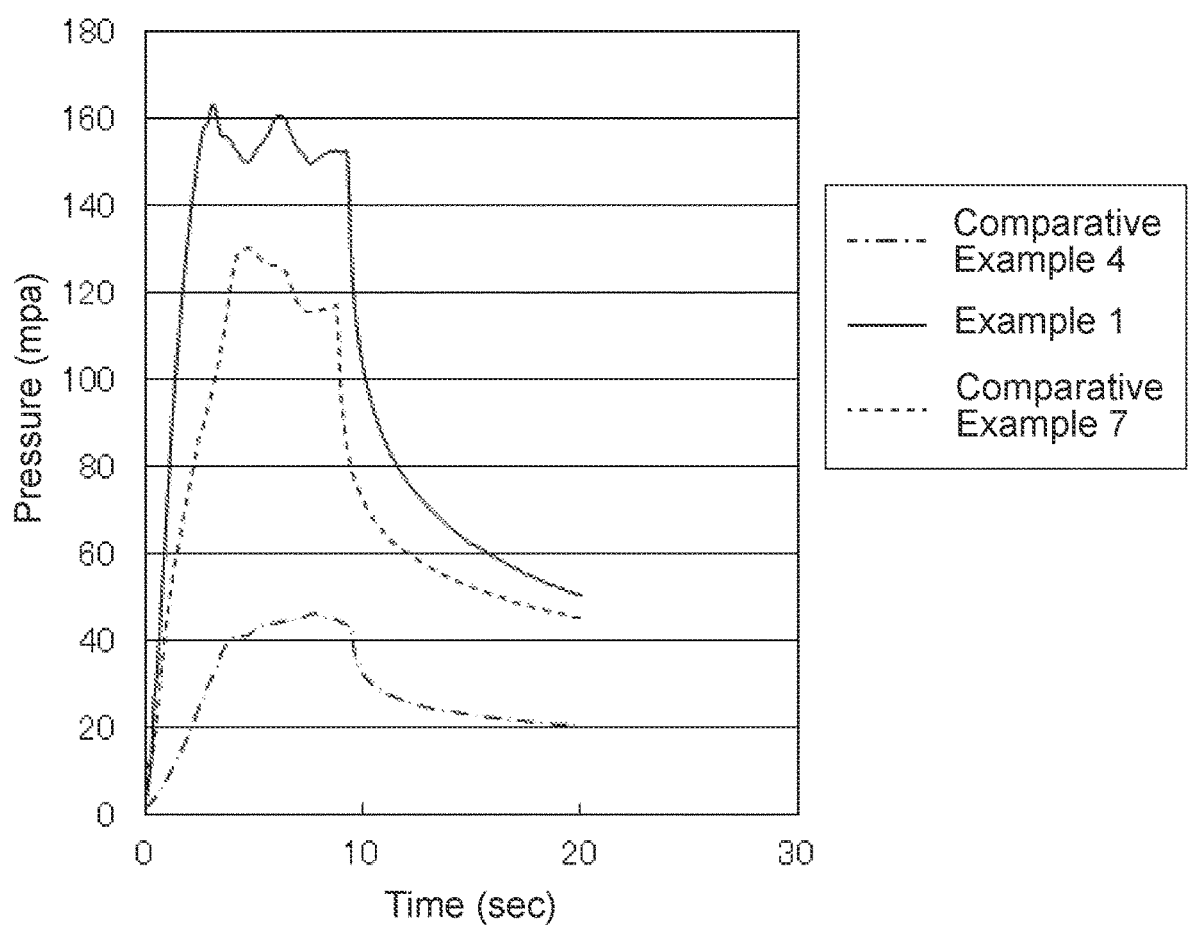
FIG. 1 is a graph for showing the results of the hardness of Example 1, Comparative Example 4, and Comparative Example 7.

Embodiments of the present invention are described below, but these embodiments are only illustrative, and needless to say, various modifications are possible without departing from the technical spirit of the present invention. A lactic acid bacterium for a lactic acid bacterium-fermented soybean foodstuff of the present invention is a novel lactic acid bacterium belonging to *Streptococcus thermophilus* and having the accession number of NITE BP-02207. The lactic acid bacterium of the present invention has a fast fermentation rate even when applied to a soybean raw material, and besides, has high fermentative activity not only under an anaerobic condition but also under an aerobic condition.

A lactic acid bacterium-fermented soybean foodstuff of the present invention comprises the lactic acid bacterium belonging to *Streptococcus thermophilus* and having the accession number of NITE BP-02207, and may be produced by inoculating a soybean raw material with the lactic acid bacterium, followed by fermentation.

A preparation method for the lactic acid bacterium is not particularly limited, but the lactic acid bacterium is preferably prepared by inoculating a soybean medium comprising a soybean raw material, which has been subjected to sterilization treatment by a conventional method and then cooled to from 30° C. to 45° C., with a predetermined amount of the lactic acid bacterium having the accession number of NITE BP-02207, followed by culturing at 30° C. to 45° C.

The soybean raw material is not particularly limited as long as the soybean raw material contains soybeans as a raw material, examples thereof include known soy milk and a liquid comprising soy flour, and the liquid comprising soy flour is preferable. When the liquid comprising soy flour is used, the liquid comprising soy flour can be satisfactorily fermented in a short period of time to provide a yogurt-like lactic acid bacterium-fermented soybean foodstuff that has a high elastic modulus and forms firm curd.

As the soy flour, known soy flour may be used without any particular limitation. Any of full-fat soybean flour, which is obtained by pulverizing whole soybeans, and defatted soybean flour may be used. In particular, sterile full-fat soybean flour obtained by pulverizing whole soybeans described in Patent Document 1 or the like is suitably used. The full-fat soybean flour obtained by pulverizing whole soybeans contains a soy pulp component, has a high nutritional value, and is rich in plant fibers, but has problems in that desired fermentation is not achieved with known lactic acid bacteria and a long fermentation time is required. However, the lactic acid bacterium of the present invention can achieve desired fermentation in a short period of time even for the full-fat soybean flour. Further, the lactic acid bacterium of the present invention can form satisfactory curd without a thickener, and enables the production of an edible lactic acid bacterium-fermented soybean foodstuff that has an extremely high nutritional value and is significantly improved also in taste evaluation for flavor, smooth texture, and the like.

As the liquid comprising soy flour to be used as the soybean raw material, an aqueous solution comprising soybean flour is suitably used, and one comprising a soybean powder material at a solid content concentration of from 7 mass % to 25 mass % and subjected to homogenization treatment and sterilization is more preferred. The firmness of the lactic acid bacterium-fermented soybean foodstuff may be adjusted by changing the solid content concentration of soybeans. In addition, a sweetener, such as sugar, a stabilizer, such as agar or gelatin, a flavor, and the like may be added before sterilization. The lactic acid bacterium of the present invention has high fermentative activity, and hence can achieve desired fermentation in a short period of time even at a low soybean solid content concentration.

Fermentation conditions are not particularly limited, and incubation may be performed in accordance with a conventional method.

An incubation temperature is not particularly limited as long as the temperature allows fermentation, but is preferably from 30° C. to 45° C. The lactic acid bacterium of the present invention has a wide optimal temperature range and takes a short fermentation time, and hence can provide a yogurt-like lactic acid bacterium-fermented soybean foodstuff by forming curd in a short period of time even at low temperature. Further, the lactic acid bacterium of the present invention can form firm curd without an additive, such as a thickener, and hence enables the production of a satisfactory lactic acid bacterium-fermented soybean foodstuff not only by a conventional pre-fermentation method involving fermentation in a tank, followed by packing into a container, but also by a post-fermentation method involving packing into a container, followed by fermentation in the container.

The lactic acid bacterium-fermented soybean foodstuff of the present invention encompasses a lactic acid bacterium-fermented soybean foodstuff obtained by fermenting a soybean raw material with the lactic acid bacterium and a foodstuff obtained by processing the lactic acid bacterium-fermented soybean foodstuff, and examples thereof include: a yogurt-like lactic acid bacterium-fermented soybean foodstuff, a frozen yogurt-like lactic acid bacterium-fermented soybean foodstuff, a cheese-like lactic acid bacterium-fermented soybean foodstuff, a sour cream-like lactic acid bacterium-fermented soybean foodstuff, and a lactic acid bacterium-fermented soybean beverage; and processed foodstuffs, such as cheesecake. Further, the lactic acid bacterium-fermented soybean foodstuff of the present invention may be used as a fermentation concentrate.

The lactic acid bacterium-fermented soybean foodstuff obtained by fermenting the soybean raw material with the lactic acid bacterium is preferably a yogurt-like lactic acid bacterium-fermented soybean foodstuff, and various yogurt-like lactic acid bacterium-fermented soybean foodstuffs may be provided by adding a sweetener, fruit, and the like to the lactic acid bacterium-fermented soybean foodstuff. The yogurt-like lactic acid bacterium-fermented soybean foodstuff has an acidity of preferably from 0.50% to 0.90%, and a pH of preferably from 4.0 to 5.0.

A processing method for the lactic acid bacterium-fermented soybean foodstuff is not particularly limited, and various fermented foodstuffs are obtained by processing the obtained lactic acid bacterium-fermented soybean foodstuff by conventional methods. For example, a cheese-like lactic acid bacterium-fermented soybean foodstuff is produced by removing soybean whey from the lactic acid bacterium-fermented soybean foodstuff in accordance with a conventional method. In addition, a sterilized lactic acid bacterium-fermented soybean beverage is produced by adding a sweetener, such as sugar, and sterilizing the resultant, in accordance with a conventional method.

EXAMPLES

The present invention is hereinafter described in more detail with Examples, but it is needless to say that Examples are only illustrative and not intended to be interpreted in a limited way.

Example 1

As lactic acid bacteria, lactic acid bacteria belonging to *Streptococcus thermophilus* and having the accession number of NITE BP-02207, which had been obtained by the following preparation method, were used.

First, a sorting step was conducted in the following manner to obtain sorted soybeans from raw material soybeans.

From 100 kg of the raw material soybeans that were prepared, foreign matters larger than soybeans (corn, mud mass, and the like) or foreign matters smaller than soybeans (grass seeds, morning glory seeds, and the like) were removed using a commercially available rough sorting machine, light foreign matters (dirt, skin, small dust, and the like) were removed using a commercially available gravity separator, foreign matters heavier than soybeans, such as stones, were removed using a commercially available stone removing machine, foreign matters having different shapes were removed using a commercially available roller sorting machine, and the resultant soybeans were sorted according to the grain size using a commercially available grain size sorting machine.

Next, a dehulling step was conducted in the following manner to obtain sterile dehulled soybeans.

After heating with hot air at a temperature of about 100° C. for about 5 minutes using a commercially available heating machine so that the temperature of the soybeans was about 60° C., the heated soybeans were subjected to a commercially available auxiliary dehulling machine (used under the following conditions: an interval between two rubber rollers was from 1 mm to 5 mm; rotation speeds of the two rubber rollers were 809 rpm for one and 1,050 rpm for the other; and a difference in rotation number thereof was about 20%) to generate cracks on the soybeans.

The soybeans having cracks were dehulled using a commercially available dehulling machine (rotation number of a plurality of blades was set to 300 rpm), and about half of the hulls dehulled were removed using a dirt collector. The remainder of dehulled hulls not removed by the dirt collector was removed by a commercially available air sorting machine.

The remaining soybean mixture after removal of the hulls was subjected to a commercially available multi-stage sieving apparatus to separate into cotyledons and germs. More specifically, the soybean mixture after the air sorting treatment was subjected to the first sieve to separate into whole soybeans not having been dehulled (undehulled whole soybeans) and a mixture of cotyledons split into two cotyledons (half-split cotyledons) and germs, and then the mixture of cotyledons and germs was subjected to the second sieve to separate into half-split cotyledons and germs.

Some hulls remained on these separated cotyledons. The separated cotyledons were cooled with room temperature air using a commercially available cooling tank (including a cooling fan and having a capacity of about 8 ms), and the cooled cotyledons were again subjected to dehulling treatment using a commercially available dehulling machine, to remove the hulls remaining on the cotyledons.

The resultant sterile dehulled soybeans were inspected for the bacterial count in accordance with the "Standard Methods of Analysis in Food Safety Regulation" (editorial supervision: the Environmental Health Bureau of the Ministry of Health and Welfare), and the bacterial count was found to be 300 cells/g or less.

The sterile dehulled soybeans were steamed with steam at a temperature of 90° C. for 120 seconds using a commercially available continuous steaming furnace.

The sterile dehulled soybeans after steaming were dried to a water content of 6 mass % using a commercially available dryer.

Using a commercially available pulverizer that had been preliminarily sterilized by heating under internal circulation of hot air at 100° C. with AEROFIN HEATER, the dried sterile dehulled soybeans were first roughly pulverized at a grain size of 30 mesh, followed by fine pulverization at a grain size of 600 mesh.

The resultant soybean powder was classified so that the soybean powder contained only grains having grain sizes of 600 mesh or less using a commercially available classifying machine. Soybean powder containing grains having grain sizes of 600 mesh or more was put again into the pulverizer.

The thus produced sterile full-fat soybean flour was used as a raw material.

A soybean flour aqueous solution containing the sterile full-fat soybean flour at a solid content concentration of 8 mass % was subjected to homogenization treatment at about 600 kgf/cm$^2$. The resultant homogenized soybean flour aqueous solution was subjected to sterilization treatment or heat sterilization treatment at 90° C. for 15 minutes and then cooled to from 30° C. to 45° C., and the resultant was used as a soybean medium.

The lactic acid bacteria were prepared by inoculating the soybean medium with a certain amount of the lactic acid bacteria having the accession number of NITE BP-02207, followed by incubation at from 45° C. to 30° C. The base sequence of the resultant lactic acid bacteria was read, and set forth in SEQ ID NO: 1 of the sequence listing. The following measurements were performed using the lactic acid bacteria.

1) Measurement of Coagulation Time under Various Incubation Conditions

The sterile soybean flour aqueous solution (solid content: 8 mass %) serving as the soybean medium using, as a raw material, the sterile full-fat soybean flour described above, a defatted soybean liquid (solid content: 8 mass %), commercially available soy milk (soybean solid content: 10 mass %, no additives), and commercially available soy milk (soybean solid content: 7 mass %, with saccharide and salt added) were each used as a medium, and aseptically inoculated and mixed with the lactic acid bacteria having the accession number of NITE BP-02207 prepared above (bacterial count: 10$^8$ cfu/mL), which served as a lactic acid bacterium starter, at a predetermined concentration (bacteria/medium: 1 mL/10 mL, 0.1 mL/10 mL, or 10 μL/10 mL) in a test tube, and each mixture was incubated under predetermined incubation temperature conditions to provide a yogurt-like lactic acid bacterium-fermented soybean foodstuff. An incubation time until coagulation was measured. The incubation conditions and the results are shown in Tables 1 to 4. A thermostatic water bath was used at the time of incubation in each of the experiments shown in Table 1 to Table 3, and a dry incubator was used in the experiment shown in Table 4.

An evaluation method for the presence or absence of coagulation was as follows: after confirmation of coagulation with eyes and confirmation by a poke with a toothpick, such firmness as to prevent a flow when the container was tilted by about 40 degrees was defined as coagulation. When the coagulation occurred, the firmness was such that the content did not fall even when the container was turned upside down. The results of the coagulation time are shown in Table 1 to Table 4.

TABLE 1

Coagulation Time

|  | Lactic acid bacterial concentration 0.1 mL/10 mL | Lactic acid bacterial concentration 10 μL/10 mL |
|---|---|---|
| Example 1 | ○ (1 hour and 40 minutes) | ○ (2 hours) |
| Comparative Example 1 | x | x |
| Comparative Example 2 | Δ (2 hours) | x (3 hours) |
| Comparative Example 3 | x (3 hours and 20 minutes) | x (3 hours and 45 minutes) |
| Comparative Example 4 | x | x |
| Comparative Example 5 | x (4 hours and 20 minutes) | x (5 hours) |
| Comparative Example 6 | x | x |

Medium: sterile soybean flour aqueous solution,
Incubation condition: temperature of 42° C.

Table 1 is a table for showing the results of the coagulation time at an incubation temperature of 42° C., using the sterile soybean flour aqueous solution (solid content: 8 mass %) as the medium. In Table 1, when the lactic acid bacterial concentration was 0.1 mL/10 mL, evaluation was performed by marking a case in which coagulation occurred in less than 2 hours with Symbol "○", marking a case in which coagulation occurred in 2 hours or more and less than 3 hours with Symbol "Δ", and marking a case in which coagulation took 3 hours or more or coagulation did not occur even after 24 hours of incubation with Symbol "x", and when the lactic acid bacterial concentration was 10 μL/10 mL, evaluation was performed by marking a case in which coagulation occurred in 2 hours or less with Symbol "○", marking a case in which coagulation occurred in more than 2 hours and less than 3 hours with Symbol "Δ", and marking a case in which coagulation took 3 hours or more or coagulation did not occur even after 24 hours of incubation with Symbol "x". A numerical value in parentheses is an incubation time until coagulation when coagulation occurred within 24 hours.

TABLE 2

Coagulation Time

|  | Incubation temperature: 37° C. | Incubation temperature: 42° C. |
|---|---|---|
| Example 1 | 30 minutes | 90 minutes |
| Comparative Example 1 | 30 minutes | 90 minutes |
| Comparative Example 2 | 120 minutes | 120 minutes |
| Comparative Example 3 | 110 minutes | 110 minutes |
| Comparative Example 4 | x | x |
| Comparative Example 5 | x | 160 minutes |

Medium: sterile soybean flour aqueous solution,
Lactic acid bacterial concentration: 1 mL/10 mL

TABLE 3

Presence or Absence of Coagulation after 16 Hours of Incubation

| Medium | Soy milk (no additives) | Soy milk (saccharide + salt) | Defatted soybean liquid | Sterile soybean flour aqueous solution |
|---|---|---|---|---|
| Example 1 | ○ | ○ | ○ | ○ |
| Comparative Example 1 | ○ | ○ | Δ | ○ |
| Comparative Example 2 | x | x | x | x |

Incubation conditions: 36° C. and 16 hours,
Lactic acid bacterial concentration: 0.1 mL/10 mL Table 3 is a table for showing the results of the coagulation time in various media at a lactic acid bacterial concentration of 0.1 mL/10 mL under the incubation conditions of 36° C. and 16 hours. In Table 3, evaluation was performed by marking a case in which complete coagulation occurred with Symbol "○", marking a case in which curd was present but significantly soft with Symbol "Δ", and marking a case in which coagulation did not occur even after 16 hours of incubation with Symbol "x".

TABLE 4

Results of Coagulation Time of Example 1 under Various Incubation Temperature Conditions

| 25° C. | 30° C. | 37° C. | 40° C. | 42° C. | 45° C. |
|---|---|---|---|---|---|
| Slight coagulation after 72 hours | 36 to 48 hours | 12 to 16 hours | 10 to 12 hours | 8 to 12 hours | 6 to 7 hours |

Medium: sterile soybean flour aqueous solution,
Lactic acid bacterial concentration: 1 mL/10 mL Table 4 is a table for showing the results of the coagulation time of Example 1 under various incubation temperature conditions using a dry incubator in an experiment for confirming an optimal temperature. At incubation temperatures of from 30° C. to 45° C., normal curds were confirmed. At an incubation temperature of 20° C., curd was not found even after 72 hours of incubation, but after subsequent incubation at 30° C. for 7 hours, curd formation was found. Thus, it was confirmed that, although in a dormant state at low temperature, the lactic acid bacteria had no injury or the like and had no problem with survival.

2) Hardness Measurement

The sterile soybean flour aqueous solution (solid content: 8 mass %), which was used as a medium, and the lactic acid bacteria having the accession number of NITE BP-02207 prepared above (bacterial count: $10^8$ cfu/mL), which served as a lactic acid bacterium starter, were packed into separate containers at a predetermined concentration (bacteria/medium: 1 mL/10 mL). After that, the medium was aseptically inoculated and mixed with the lactic acid bacteria, and the resultant was incubated in a thermostatic water bath at 37° C. to provide a yogurt-like lactic acid bacterium-fermented soybean foodstuff. An incubation time until coagulation was measured. The results of the coagulation time are shown in Table 5. In addition, the resultant yogurt-like lactic acid bacterium-fermented soybean foodstuff was put into a refrigerator so that its temperature became around 10° C., and then its hardness was measured with a rheometer. The results of the hardness are shown in FIG. 1.

TABLE 5

|  | Coagulation time |
| --- | --- |
| Example 1 | ○ |
| Comparative Example 4 | x |
| Comparative Example 7 | Δ |

In Table 5, evaluation was performed by marking a case in which the incubation time until coagulation was 130 minutes or less with Symbol "○", marking a case in which the incubation time until coagulation was more than 130 minutes and 4 hours or less with Symbol "Δ", and marking a case in which coagulation did not occur even after 4 hours of incubation with Symbol "x".

3) Measurement of pH and Acidity

The sterile soybean flour aqueous solution (solid content: 8 mass %) was used as a medium, and aseptically inoculated and mixed with the lactic acid bacteria having the accession number of NITE BP-02207 prepared above (bacterial count: $10^8$ cfu/mL), which served as a lactic acid bacterium starter, at a predetermined concentration (bacteria/medium: 1 mL/10 mL) in test tubes, followed by incubation in a thermostatic water bath at 37° C. Each of the test tubes was put into a refrigerator when yogurt-like curd was formed (solidification) therein to stop fermentation, followed by measurement of acidity and pH. An instrument used in the pH measurement is HORIBA pH Meter D-71. In addition, the acidity measurement was performed by a titration method with 0.1 N Na hydroxide in conformity to Ministerial Ordinance on Milk and Milk products Concerning Compositional Standards, etc. The results are shown in Table 6.

TABLE 6

|  | Acidity (%) | pH |
| --- | --- | --- |
| Example 1 | 0.33 | 5.17 |
| Comparative Example 1 | 0.27 | 5.33 |
| Comparative Example 2 | 0.20 | 6.00 |
| Comparative Example 3 | 0.24 | 5.88 |
| Comparative Example 4 | 0.18 | 6.57 |
| Comparative Example 5 | 0.20 | 6.44 |

NC (medium: soybean flour aqueous solution), pH 6.71

Comparative Examples 1 and 2

Experiments were performed by the same method as in Example 1 except that the following known lactic acid bacteria were used as the lactic acid bacteria: a *Streptococcus thermophilus* strain NBRC13957 (Comparative Example 1) and a *Streptococcus thermophilus* strain NBRC111149 (Comparative Example 2). The results are shown in Tables 1 to 3 and 6.

Comparative Examples 3 to 7

Experiments were performed by the same method as in Example 1 except that *Streptococcus thermophilus* bacteria each separated from commercially available yogurt were used as the lactic acid bacteria. The results are shown in Tables 1 to 3, 5, and 6. In each of Comparative Examples 4 and 5, after the incubation in the measurement of pH and acidity, required curd was not obtained, though solidification occurred.

Experimental Example 1 and Comparative Experimental Examples 1 to 5

As Experimental Example 1, the following saccharide fermentability test was performed using lactic acid bacteria having the accession number of NITE BP-02207 prepared by the same method as in Example 1.

In Comparative Experimental Examples 1 to 3, *Streptococcus thermophilus* bacteria respectively separated from three commercially available products of yogurt (commercially available strain A to strain C) were used as the lactic acid bacteria. In Comparative Experimental Examples 4 and 5, experiments were performed by the same method as in Example 1 except that the following known lactic acid bacteria were used as the lactic acid bacteria: a *Streptococcus thermophilus* strain NBRC13957 (Comparative Experimental Example 4) and a *Streptococcus thermophilus* strain NBRC111149 (Comparative Experimental Example 5).

1) Saccharide Fermentability Test (Anaerobic Condition and Aerobic Condition)

Through the use of API 50 CHL (medium for *Lactobacillus*, manufactured by Sysmex bioMérieux Co., Ltd.) and API 50 CH (substrate plate for research, manufactured by Sysmex bioMérieux Co., Ltd.), saccharide fermentability was investigated on the basis of methods described in the kits. For an anaerobic condition, a mineral oil (manufactured by Sysmex bioMérieux Co., Ltd.) was overlaid in an upper portion of a cup in order to prevent contact with air. For an aerobic condition, a bacterial suspension was poured up to the upper portion of the cup so that the bacterial suspension was brought into contact with air. Results of incubation at 36° C. for 48 hours are shown. In Tables 7 to 9, results obtained under the anaerobic condition are shown, and in Tables 10 to 12, results obtained under the aerobic condition are shown. The details of each saccharide item serving as a substrate shown in the tables are as described below.

cont.: control, GLY: glycerol, ERY: erythritol, DARA: D-arabinose, LARA: L-arabinose, RIB: D-ribose, DXYL: D-xylose, LXYL: L-xylose, ADO: D-adonitol, MDX: methyl-α-D-xylopyranoside, GAL: D-galactose, GLU: D-glucose, FRU: D-fructose, MNE: D-mannose, SBE: L-sorbose, RHA: L-rhamnose, DUL: dulcitol, INO: inositol, MAN: D-mannitol, SOR: D-sorbitol, MDM: methyl-α-D-mannopyranoside, MDG: methyl-α-D-glucopyranoside, NAG: N-acetylglucosamine, AMY: amygdalin, ARB: arbutin, ESC: esculin, iron citrate, SAL: salicin, CEL: D-cellobiose, MAL: D-maltose, LAC: D-lactose, MEL: D-melibiose, SAC: D-sucrose, TRE: D-trehalose, INU: inulin, MLZ: D-melezitose, RAF: D-raffinose, Starch: starch, GLYG: glycogen, XLT: xylitol, GEN: gentiobiose, TUR: D-turanose, LYX: D-lyxose, TAG: D-tagatose, DFUC: D-fucose, LFUC: L-fucose, DARL: D-arabitol, LARL: L-arabitol, GNT: potassium gluconate, 2 KG: potassium 2-ketogluconate, 5 KG: potassium 5-ketogluconate.

TABLE 7

| Substrate | cont. | GLY | ERY | DARA | LARA | RIB | DXYL | LXYL | ADO | MDX | GAL | GLU | FRU | MNE | SBE | RHA | DUL |
|---|---|---|---|---|---|---|---|---|---|---|---|---|---|---|---|---|---|
| Experimental Example 1 | − | − | − | − | − | − | − | − | − | − | − | + | + | − | − | − | − |
| Comparative Experimental Example 1 | − | − | − | − | − | − | − | − | − | − | − | + | − | − | − | − | − |
| Comparative Experimental Example 2 | − | − | − | − | − | − | − | − | − | − | − | + | − | − | − | − | − |
| Comparative Experimental Example 3 | − | − | − | − | − | − | − | − | − | − | − | + | − | − | − | − | − |
| Comparative Experimental Example 4 | − | − | − | − | − | − | − | − | − | − | − | + | ± | ± | − | − | − |
| Comparative Experimental Example 5 | − | − | − | − | − | − | − | − | − | − | ± | + | + | ± | − | − | − |

TABLE 8

| Substrate | INO | MAN | SOR | MDM | MDG | NAG | AMY | ARB | ESC | SAL | CEL | MAL | LAC | MEL | SAC | TRE | INU |
|---|---|---|---|---|---|---|---|---|---|---|---|---|---|---|---|---|---|
| Experimental Example 1 | − | − | − | − | − | − | − | − | − | − | − | + | − | − | + | − | − |
| Comparative Experimental Example 1 | − | − | − | − | − | − | − | − | − | − | − | + | − | − | + | − | − |
| Comparative Experimental Example 2 | − | − | − | − | − | − | − | − | − | − | − | + | − | − | + | − | − |
| Comparative Experimental Example 3 | − | − | − | − | − | − | − | − | − | − | − | + | − | − | + | − | − |
| Comparative Experimental Example 4 | − | − | − | − | − | − | − | − | − | − | − | − | − | − | + | − | − |
| Comparative Experimental Example 5 | − | − | − | − | − | − | − | − | − | − | − | ± | + | − | + | − | − |

TABLE 9

| Substrate | MLZ | RAF | Starch | GLYG | XLT | GEN | TUR | LYX | TAG | DFUC | LFUC | DARL | LARL | GNT | 2KG | 5KG |
|---|---|---|---|---|---|---|---|---|---|---|---|---|---|---|---|---|
| Experimental Example 1 | − | − | − | − | − | − | − | − | − | − | − | − | − | − | − | − |
| Comparative Experimental Example 1 | − | − | − | − | − | − | − | − | − | − | − | − | − | − | − | − |
| Comparative Experimental Example 2 | − | − | − | − | − | − | − | − | − | − | − | − | − | − | − | − |
| Comparative Experimental Example 3 | − | − | − | − | − | − | − | − | − | − | − | − | − | − | − | − |
| Comparative Experimental Example 4 | − | − | − | − | − | − | − | − | − | − | − | − | − | − | − | − |
| Comparative Experimental Example 5 | − | − | − | − | − | − | − | − | − | − | − | − | − | − | − | − |

TABLE 10

| Substrate | cont. | GLY | ERY | DARA | LARA | RIB | DXYL | LXYL | ADO | MDX | GAL | GLU | FRU | MNE | SBE | RHA | DUL |
|---|---|---|---|---|---|---|---|---|---|---|---|---|---|---|---|---|---|
| Experimental Example 1 | − | − | − | − | − | − | − | − | − | − | − | ± | − | − | − | − | − |
| Comparative Experimental Example 1 | − | − | − | − | − | − | − | − | − | − | − | ± | − | − | − | − | − |
| Comparative Experimental Example 2 | − | − | − | − | − | − | − | − | − | − | − | + | − | − | − | − | − |
| Comparative Experimental Example 3 | − | − | − | − | − | − | − | − | − | − | − | ± | − | − | − | − | − |
| Comparative Experimental Example 4 | − | − | − | − | − | − | − | − | − | − | − | + | − | − | − | − | − |
| Comparative Experimental Example 5 | − | − | − | − | − | − | − | − | − | − | ± | + | + | ± | − | − | − |

TABLE 11

| Substrate | INO | MAN | SOR | MDM | MDG | NAG | AMY | ARB | ESC | SAL | CEL | MAL | LAC | MEL | SAC | TRE | INU |
|---|---|---|---|---|---|---|---|---|---|---|---|---|---|---|---|---|---|
| Experimental Example 1 | − | − | − | − | − | − | − | − | − | − | − | − | ± | − | + | − | − |
| Comparative Experimental Example 1 | − | − | − | − | − | − | − | − | − | − | − | − | ± | − | ± | − | − |
| Comparative Experimental Example 2 | − | − | − | − | − | − | − | − | − | − | − | − | ± | − | ± | − | − |
| Comparative Experimental Example 3 | − | − | − | − | − | − | − | − | − | − | − | − | ± | − | ± | − | − |
| Comparative Experimental Example 4 | − | − | − | − | − | − | − | − | − | − | − | − | ± | − | ± | − | − |
| Comparative Experimental Example 5 | − | − | − | − | − | − | − | − | − | − | − | − | ± | − | + | − | − |

TABLE 12

| Substrate | MLZ | RAF | Starch | GLYG | XLT | GEN | TUR | LYX | TAG | DFUC | LFUC | DARL | LARL | GNT | 2KG | 5KG |
|---|---|---|---|---|---|---|---|---|---|---|---|---|---|---|---|---|
| Experimental Example 1 | − | − | − | − | − | − | − | − | − | − | − | − | − | − | − | − |
| Comparative Experimental Example 1 | − | − | − | − | − | − | − | − | − | − | − | − | − | − | − | − |
| Comparative Experimental Example 2 | − | − | − | − | − | − | − | − | − | − | − | − | − | − | − | − |
| Comparative Experimental Example 3 | − | − | − | − | − | − | − | − | − | − | − | − | − | − | − | − |
| Comparative Experimental Example 4 | − | − | − | − | − | − | − | − | − | − | − | − | − | − | − | − |
| Comparative Experimental Example 5 | − | − | − | − | − | − | − | − | − | − | − | − | − | − | − | − |

In Tables 7 to 12, +, ±, and − show the following results, respectively: color change to yellow; color change to green or yellowish green; and no color change (remaining bluish purple).

It is said that sucrose accounts for most of the saccharides contained in soybeans. As shown in Table 8, under the anaerobic condition, all the bacterial strains fermented sucrose (SAC). In addition, as shown in Table 11, under the aerobic condition, only Experimental Example 1 using the lactic acid bacterium of the present invention and Comparative Experimental Example 5 using the bacterial strain NBRC 111149 satisfactorily produced an acid from sucrose (SAC).

2) Absorbance Measurement 2-1)

Figure 2:
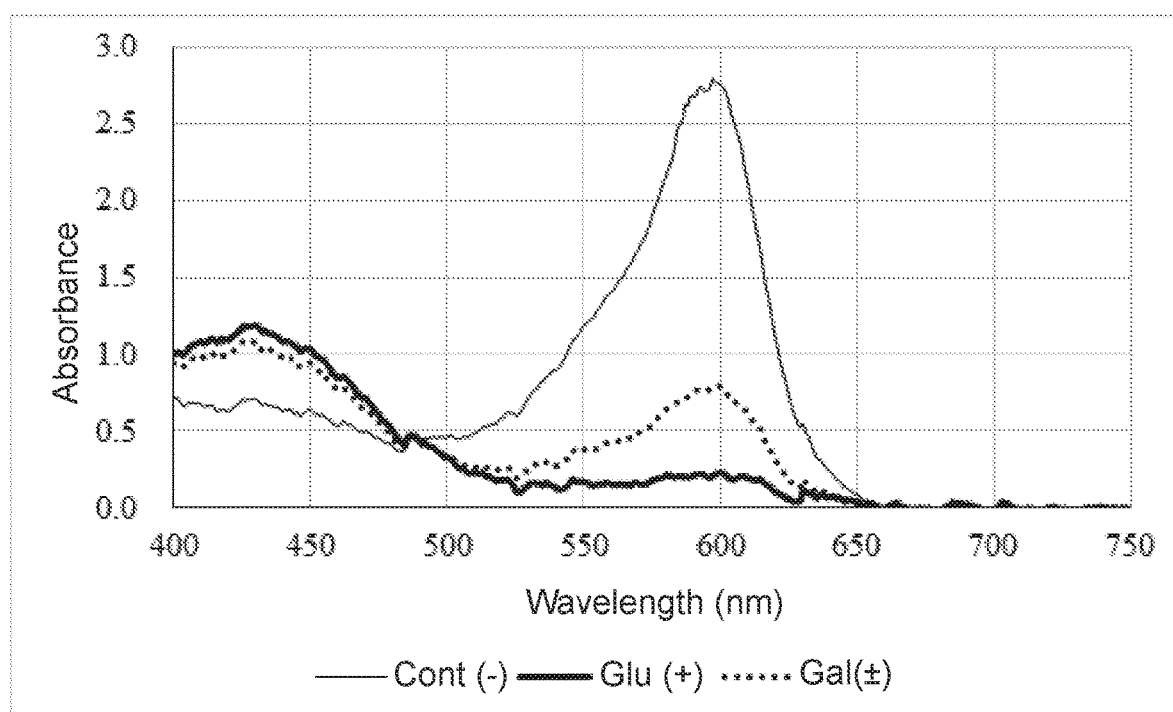
FIG. 2 is a graph for showing the results of absorbance measurement of Comparative Experimental Example 5.

An investigation was made into the quantification of the degree of color change in the saccharide fermentability test. Three specimens [Cont.: − (bluish purple), GAL: ± (green), and GLU: + (yellow)] after the saccharide fermentability test of Comparative Experimental Example 5 under the aerobic condition were measured for absorption spectra in a visible light region. The results are shown in FIG. 2.

It was found that Cont. without fermentation (−) had an absorbance peak at a wavelength of 600 nm, GLU with fermentation (+) had an absorbance peak at a wavelength of 430 nm, and a numerical value for $A_{430}/A_{600}$ increased with the progress of fermentation. Numerical values for $A_{430}/A_{600}$ are shown below.

Bluish purple (−: 0.3), green (±: 1.4), and yellow (+: 5.0)

2-2)

SAC specimens after the saccharide fermentability test under the aerobic condition were used and measured for absorption spectra in the visible light region, and fermentative activity for sucrose (SAC) under the aerobic condition was evaluated on the basis of a numerical value for $A_{430}/A_{600}$. The results are shown in Table 13.

TABLE 13

|  | $A_{430}/A_{600}$ | Color tone |
| --- | --- | --- |
| Experimental Example 1 | 3.2 | Yellow |
| Comparative Experimental Example 1 | 2.0 | Green |
| Comparative Experimental Example 2 | 1.1 | Green |
| Comparative Experimental Example 3 | 1.2 | Green |
| Comparative Experimental Example 4 | 1.5 | Green |
| Comparative Experimental Example 5 | 2.8 | Yellow |

As shown in Table 13, Experimental Example 1 using the lactic acid bacterium of the present invention had the highest result. The above-mentioned tests revealed that the lactic acid bacterium of the present invention had high fermentative activity even under the aerobic condition.

Example 2 and Comparative Examples 8 to 12

In Example 2, the following experiment was performed using lactic acid bacteria having the accession number of NITE BP-02207 prepared by the same method as in Example 1. The sterile soybean flour aqueous solution (solid content: 8 mass %) serving as the soybean medium using, as a raw material, the sterile full-fat soybean flour used in Example 1 was used as a medium.

In Comparative Examples 8 to 10, the commercially available strain A to strain C used in Experimental Examples 1 to 3 described above were used as lactic acid bacteria. In Comparative Examples 11 and 12, the following known lactic acid bacteria were used as the lactic acid bacteria: a *Streptococcus thermophilus* strain NBRC13957 (Comparative Example 11) and a *Streptococcus thermophilus* strain NBRC111149 (Comparative Example 12).

1) pH Test

A preincubated broth of each kind of bacterial cells was taken in an amount corresponding to about $10^7$ cells, suspended in 5 mL of the soybean medium, and incubated in a container at 42° C. for 4 hours to provide a fermentation product. After that, a pH was measured at each of the upper surface of the container and the bottom surface of the container. The state and pH measurement values of the fermentation product are shown in Table 14.

TABLE 14

|  | pH at upper surface of container | pH at bottom surface of container | State | Elastic modulus (Pa) |
| --- | --- | --- | --- | --- |
| Example 2 | 4.76 | 4.63 | Solid | 32,301 |
| Comparative Example 8 | 5.22 | 5.04 | Solid | 2,640 |
| Comparative Example 9 | 5.95 | 5.34 | Solid/Liquid | — |
| Comparative Example 10 | 5.56 | 5.34 | Solid/Liquid | — |
| Comparative Example 11 | 5.80 | 5.56 | Liquid | — |
| Comparative Example 12 | 5.63 | 5.52 | Liquid | — |

As shown in Table 14, Example 2 using the lactic acid bacterium of the present invention recorded the lowest pH values at both the upper surface and the bottom surface. Except in Example 2, the pH tended to lower less significantly at the upper surface of the container than at the bottom surface, but in Example 2, the pH satisfactorily lowered at both the upper surface and the bottom surface of the container. Thus, it was found that the lactic acid bacterium of the present invention satisfactorily caused fermentation even in the presence of oxygen. It was only Example 2 using the lactic acid bacterium of the present invention and Comparative Example 8 using the commercially available strain A that solidified into a yogurt form.

2) Elastic Modulus Measurement

The elastic modulus of each of the fermentation products of Example 2 and Comparative Example 8, which solidified into a yogurt form in the 1) pH Test, was measured. The elastic modulus was measured with a creep tester from Yamaden Co., Ltd. (product name: Rheoner RE33005). The results are shown in Table 14.

As shown in Table 14, Example 2 using the lactic acid bacterium of the present invention showed a numerical value 12 or more times higher than that of Comparative Example 8 using the commercially available strain A.

Example 3

Yogurt-like lactic acid bacterium-fermented soybean foodstuffs were obtained by the same method as in Example 2 except that the incubation conditions were changed to the following.

Incubation was performed at 42° C. for 8 hours using commercially available soy milk (soybean solid content: 7 mass % and 8 mass %) as a medium. As a result, the soy milk solidified into a yogurt form. The elastic modulus of each of the resultant yogurt-like lactic acid bacterium-fermented soybean foodstuffs was measured. The results are shown in Table 15.

TABLE 15

| Example 3 | |
|---|---|
| | Elastic modulus (Pa) |
| 7% soy milk | 3,876 |
| 8% soy milk | 5,429 |

As shown in Table 15, a higher elastic modulus was shown at a soybean solid content concentration of the soy milk of 8 mass % than at 7 mass %, but the numerical value was about one sixth of the elastic modulus of Example 2 produced using the soybean powder solution. The soy milk also solidified into a yogurt form, but it was revealed that the gel was brittle even when incubated for a longer period of time than in the case of using the soybean medium.

Example 4

The following experiment was performed using, as the lactic acid bacteria, lactic acid bacteria having the accession number of NITE BP-02207 prepared by the same method as in Example 1.

Sterile full-fat soybean flour produced by the same method as in Example 1 was used as a raw material, and a soybean flour aqueous solution containing the sterile full-fat soybean flour at a predetermined concentration (5 mass %, 10 mass %, and 15 mass % in terms of soybean solid content concentration) was subjected to homogenization treatment at from 500 kgf/cm² to 600 kgf/cm². The resultant homogenized soybean flour aqueous solution was subjected to sterilization treatment by heating at 90° C. for 15 minutes and then cooled to from 30° C. to 45° C., and the resultant was used as a soybean medium.

The lactic acid bacteria were added as a starter to the soybean medium at a predetermined concentration ($10^8$ cells/mL), and incubated in a dry incubator at 37° C. or 42° C. for 30 minutes to provide a fermentation product. The fermentation product is hereinafter referred to as fermented milk.

1) Presence or Absence of Coagulation

For the fermented milk obtained above, the presence or absence of coagulation was confirmed by the same method as in Example 1. In addition, as a control, an experiment was performed by the same method except that no lactic acid bacteria were added. The results are shown in Table 16. In the table, ○ represents the presence of coagulation, and x represents the absence of coagulation.

TABLE 16

| Example 4 Presence or Absence of Coagulation | | | | |
|---|---|---|---|---|
| Incubation temperature (° C.) | Addition of lactic acid bacteria | Soybean solid content concentration | | |
| | | 5 mass % | 10 mass % | 15 mass % |
| 37 | Present | ○ | ○ | ○ |
| 37 | Absent | x | x | x |
| 42 | Present | ○ | ○ | ○ |
| 42 | Absent | x | x | x |

As shown in Table 16, at both 37° C. and 42° C., coagulation occurred in 30 minutes within the soybean solid content concentration range of from 5 mass % to 15 mass %, indicating that the lactic acid bacterium of the present invention caused curdling in an extremely short fermentation time.

2) Sensory Test (Sourness)

The fermented milk obtained above was subjected to a sensory test for sourness. In addition, as a control, an experiment was performed by the same method except that no lactic acid bacteria were added. The results are shown in Table 17. In the table, judging criteria are as described below.

○: Moderate sourness is felt, x: Sourness is hardly felt.

TABLE 17

| Example 4 Sensory Test (Sourness) | | | | |
|---|---|---|---|---|
| Incubation temperature (° C.) | Addition of lactic acid bacteria | Soybean solid content concentration | | |
| | | 5 mass % | 10 mass % | 15 mass % |
| 37 | Present | ○ | ○ | ○ |
| 37 | Absent | x | x | x |
| 42 | Present | ○ | ○ | ○ |
| 42 | Absent | x | x | x |

As shown in Table 17, the fermented milk obtained using the lactic acid bacterium of the present invention had moderate sourness that was felt in all the cases.

3) Sensory Test (Firmness)

The fermented milk obtained above was subjected to a sensory test for firmness. The results are shown in Table 18.

TABLE 18

| Example 4 Sensory Test (Firmness) | | | | |
|---|---|---|---|---|
| Incubation temperature (° C.) | Addition of lactic acid bacteria | Soybean solid content concentration | | |
| | | 5 mass % | 10 mass % | 15 mass % |
| 37 | Present | Soft | Moderate elastic force | Firm |
| 42 | Present | Soft | Moderate elastic force | Firm |

As shown in Table 18, a difference in soybean solid content concentration of the soybean medium resulted in a difference in firmness, the fermented milk using the soybean medium having a soybean solid content concentration of 5 mass % was suitable for a lactic acid bacterium-fermented soybean beverage, the fermented milk using the soybean medium having a soybean solid content concentration of 10 mass % was suitable for a yogurt-like lactic acid bacterium-fermented soybean foodstuff, and the fermented milk using the soybean medium having a soybean solid content concentration of 15 mass % was suitable for a cheese-like lactic acid bacterium-fermented soybean foodstuff.

Example 5

Yogurt-like lactic acid bacterium-fermented soybean foodstuffs were obtained by fermenting a soybean medium with lactic acid bacteria by the same method as in Example 4 except that the soybean solid content concentration of the soybean medium was changed to 8 mass %, 9 mass %, and 10 mass %. Each of the resultant yogurt-like lactic acid bacterium-fermented soybean foodstuffs had moderate sourness, moderate elasticity, and smooth texture, and hence was an excellent yogurt-like lactic acid bacterium-fermented soybean foodstuff.

Example 6

With the use of a soybean medium having a soybean solid content concentration of 15 mass %, fermented milk was obtained by fermenting the soybean medium with lactic acid bacteria by the same method as in Example 4. The resultant fermented milk was used, and whey was removed therefrom in accordance with a conventional method, to thereby produce a cheese-like lactic acid bacterium-fermented soybean foodstuff. The resultant cheese-like lactic acid bacterium-fermented soybean foodstuff did not have an unpleasant soybean odor that was felt, and had moderate sourness, elasticity appropriate for cheese, and smooth texture, and hence was an excellent cheese-like lactic acid bacterium-fermented soybean foodstuff.

Example 7

With the use of a soybean medium having a soybean solid content concentration of 5 mass %, fermented milk was obtained by fermenting the soybean medium with lactic acid bacteria by the same method as in Example 4. The resultant fermented milk was used, a stabilizer and sugar were mixed therewith, and the mixture was homogenized in accordance with a conventional method, to thereby produce a lactic acid bacterium-fermented soybean beverage. The resultant lactic acid bacterium-fermented soybean beverage had moderate sourness and smooth sensation in the throat as a beverage, and hence was an excellent lactic acid bacterium-fermented soybean beverage.

The invention claimed is:

1. A production method for a lactic acid bacterium-fermented soybean foodstuff, comprising a step of fermenting soybean milk with *Streptococcus thermophilus* strain NITE BP-02207.

2. The production method according to claim 1, wherein the lactic acid bacterium-fermented soybean foodstuff is soybean yogurt comprising the *Streptococcus thermophilus* strain NITE BP-02207.

3. The production method according to claim 2, wherein the soybean yogurt has an acidity of 0.5-0.9 wt. %.

4. The production method according to claim 2, wherein the soybean yogurt has a pH of 4.0 to 5.0.

* * * * *